US006489094B2

(12) United States Patent
Ekins et al.

(10) Patent No.: US 6,489,094 B2
(45) Date of Patent: Dec. 3, 2002

(54) METHOD AND DEVICE FOR DRUG-DRUG INTERACTION TESTING SAMPLE PREPARATION

(75) Inventors: Sean Ekins, Indianapolis, IN (US); Diane Lynn Johnson, Waterford, CT (US); Kevin George Kelly, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 3 days.

(21) Appl. No.: 09/858,972

(22) Filed: May 16, 2001

(65) Prior Publication Data

US 2001/0049092 A1 Dec. 6, 2001

Related U.S. Application Data

(60) Provisional application No. 60/208,213, filed on May 31, 2000.

(51) Int. Cl.[7] ........................ C12Q 1/00; G01N 33/567; C12M 1/34; C12M 3/00

(52) U.S. Cl. ....................... 435/4; 435/7.21; 435/287.1; 435/288.4

(58) Field of Search ........................ 435/4, 7.21, 287.1, 435/288.4

(56) References Cited

U.S. PATENT DOCUMENTS 6,124,282 A * 9/2000 Sellers et al.

OTHER PUBLICATIONS

Chauret et al. (Anal. Biochem. (Dec. 15, 1999) 276 (2) 215–26).*

* cited by examiner

*Primary Examiner*—Christopher R. Tate
(74) *Attorney, Agent, or Firm*—Peter C. Richardson; Paul H. Ginsburg; Israel Nissenbaum

(57) ABSTRACT

A method and device for the automated large scale preparation for testing of drug-drug interactions, particularly with determination of $IC_{50}$ and Ki, as a screening tool enhancement for determining viability of large numbers of compounds as drug candidates. Small samples of specific probe substrates and new compound inhibitors are automatically dispensed en masse into multi-welled reaction plates which are prefilled with thawed human microsomes, buffer and cofactor. The reaction plates are incubated and the reaction products are tested within degradation time limits, for initial biological determinations of relevant interaction effects of the compounds. The device used for the preparations comprises computer controlled multiple liquid handling cannulas, micropipetting members, refrigeration, freezer and temperature controlled incubator units, vacuum filtration device, bar code tracking of the plates, transport mechanisms for movement and manipulation of multiwell plates and sample mixing elements with coordinated timing of all operations within limited time frame testing parameters.

3 Claims, 3 Drawing Sheets

18
100
11b
13
12
14
15
11a
12
13
30j
16
21
17
10
20

METHOD AND DEVICE FOR DRUG-DRUG INTERACTION TESTING SAMPLE PREPARATION

This application claims the benefit o U.S. Provisional Application No. 60/208,213, filed May 31, 2000.

FIELD OF THE INVENTION

This invention relates to an improved in vitro method for determining the potential for drug-drug interaction involving cytochrome P450s (CYP) with new chemical entities. This invention further relates to the in vitro determination testing of in vivo drug-drug interactions, particularly as they affect liver metabolism, as an initial or primary screen for compounds as drug candidates.

BACKGROUND OF THE INVENTION

Unfavorable drug-drug interactions (DDI) are responsible for approximately 1–2% of clinically relevant DDI, which while a relatively small number, are nevertheless an important factor in determining whether a new chemical entity will successfully make it beyond a drug discovery program to development. In addition, the late discovery of a clinically significant drug-drug interaction (which would likely eliminate a drug from use) for an otherwise promising candidate could result in the significant economic waste of testing resources already expended on a project.

It is therefore important to screen for potential interactions early on, as well as to select the most appropriate in vivo studies. In this regard, drug interactions with cytochrome P450s (CYPs) are particularly important. CYP1A2, CYP2C, CYP2D6 and CYP3A4 represent greater than 90% of total hepatic P450 and nearly 80% of therapeutic drugs are metabolized by these same enzymes. Interaction with one or more of these enzymes in vivo would pose a potentially relevant event in the clinic. Recently, it has been established that in vitro systems have proven capable of predicting the likelihood of DDI as they allow identification of the CYPs responsible for metabolism as well as determination of the relative contribution to overall elimination of the inhibited pathways.

Since the number of molecules synthesized by pharmaceutical companies has dramatically increased with the utilization of combinatorial chemistry, there is now a shift in emphasis towards earlier implementation of higher throughput in vitro studies for metabolism or lead optimization. The prediction of drug-drug interactions of new chemical entities (NCEs) using in vitro methods, such as human microsomes (HLMs), hepatocytes or individual expressed CYPs has escalated both in importance and scale of use, as one way to reliably avoid potential interactions in vivo.

Actual DDI testing, such as determination of $IC_{50}$ or Ki values, is relatively efficient and rapid. It is however, the preparation of the samples, to provide valid in vitro results that is the most exacting portion of the testing protocol and it is such preparation, within rigid short time limit constraints (as a function of testing material degradation), available personnel, equipment, and limited amount of material (microsome, compound samples, etc.), that has limited increased scale-up of initial evaluations and screening of compounds.

Current methodologies involving manual test sample preparation have proven inadequate with respect to increased throughput. A major factor for such inadequacy is the instability of the testing materials, particularly the microsomes which tend to decrease in activity by approximately one hour after being thawed and incubated from freezer storage. Unless the preparation, timing and testing are carefully controlled and coordinated, inaccurate results are likely to be obtained from materials that have not been prepared and tested within the available time window before significant loss of enzyme activity occurs.

Furthermore, due to the vast number of compounds to be tested for initial screening, it is viable to synthesize only small quantities of the compounds for such initial testing. In addition, there is the availability of only limited amounts of microsomes for the testing of the vastly increased number of compounds as would be required for the increased throughput. Accordingly, in addition to the time coordination required for scaled up testing, there is a need for adequately obtaining accurate test results with limited availability of testing materials.

Currently, manual preparations for determinations of DDI in vitro, are gaining in speed and efficiency through the use of 96 and 384 well plates and multi-well pipetting of test sample material. However, other operations of thawing of samples, incubation, plate transport, mixing, etc. are still done manually, with attendant problems of timing and coordination which limit the number of testing samples which can be reliably prepared.

At least four test plates are used in a single testing procedure or run (for compound/CYP enzyme substrate, reaction, filtration and collection) that involve the steps of thawing, preparation, incubation, mixing, and processing of inhibitor compounds being tested (NCEs) with a particular probe (cytochrome P450-specific substrates) and thawed microsomes which are buffered and provided with cofactor. Coordination and efficiency of handling of the various plates during processing is exponentially more difficult with the increased number of compounds being tested and the short time frame allowed for processing which does not change with the increase of tests for which the compounds are prepared.

SUMMARY OF THE INVENTION

It is accordingly an object of the present invention to provide an efficient time-coordinated automated system for preparing a large number of drug candidate compounds for drug-drug interactions testing as an initial screen for viability, within the time constraints of material degradation. Preparation includes the operations of material thawing and incubation, test well filling, mixing (with attendant reactions), and vacuum filtration and coordinated test plate transport to operational stations.

It is a further object of the present invention to provide a system which automatically effects the continuous requisite steps of preparation and test well filling with HLM (after thawing, buffering and addition of co-factor), addition of CYP-specific probe substrates and inhibitor compounds (NCEs) to be tested and controls; incubation, mixing, test tray or plate handling and transport to preparation, operation and testing stations, all within a time window needed, prior to actual testing, before the onset of material degradation.

It is still yet another object of the present invention to effectively minimize test sample amounts, particularly with availability of only small amounts of synthesized inhibitor compound samples and microsomes, by enhancing testing intra and inter reproducibility of standards and particularly with automated single concentration testing of compounds and enzymes.

Co-pending provisional application no. 60/193,717, filed Mar. 31, 2000, describes the use of single point concentrations for effective DDI determinations. The disclosure thereof is included herein in its entirety by reference thereto, which disclosure already minimizes the need for materials with attendant speed in obtaining results without any significant loss of accuracy in obtaining viable results and which utilization is further enhanced by the automation thereof.

It is another object of the present invention to provide a fully operational test preparation system which is self operable to the limits of its storage capacity of processed components and materials, without manual intervention.

Generally the present invention comprises a synchronized, time coordinated method and device for the fully automated multiple-plate in vitro preparation of compounds which are candidates for drugs (NCEs), for drug-drug interaction testing, particularly for testing involving cytochrome P450 (CYP), CYP1A2, CYP2C9, CYP2C19, CYP2D6 and CYP3A4, as a step screening for viability in mammals and particularly humans. To facilitate the time coordinated preparation, non-degrading elements involved in the preparation are made ready prior to an actual test run with degrading materials such as microsomes. Thus, generally stable candidate compounds (NCEs) are preferably pre-mixed in multi-well plates with the CYP-specific probe substrates in the requisite permutations and combinations, for use during the test specimen preparation and reactions with the microsomes.

The method of the present invention comprises processing of one, and preferably offset or tandem pairs of testing plates, in a test run, of a predetermined number of single or test plate pairs, with the automated steps of:

a) retrieving frozen microsome samples from a freezer storage unit (with a storage condition of about −20° C.), with a timed, automated mechanical transport mechanism, to a thawing site or unit (in a lesser preferred embodiment the temperature of the freezer unit itself is elevated to thawing conditions-without need for transport);

b) defrosting or thawing the frozen microsome samples, such as by exposure to 4° C. ambient conditions and combining a measured portion (e.g., aliquot) of the thawed microsome samples with cofactor (e.g., NADPH and regenerating system) and buffer into a substantially homogenous mixture (M/C/B);

c) mechanically introducing (such as by aliquoting) a predetermined quantity of the combination (M/C/B) into each of individual wells of a multiwell reaction plate and preferably pre-incubating the combination;

d) automatically mechanically combining (such as by aliquot introduction) the (M/C/B) samples in the wells of the reaction plate with S/I solutions of preselected CYP specific probe substrate and inhibitor compounds (NCEs);

e) incubating the reaction plate with contained microsome samples (M/C/B), preselected CYP-specific probe substrate and inhibitor compounds (NCEs), to 37° C. (for humans or other in vivo emulation condition for the particular mammal) for a pre-determined period of time to effect a reaction with resultant reaction products;

f) stopping any reactions which occur, at the end of the pre-determined period of time, purifying reaction products and using the reaction products in an analysis test for determining the extent of any drug-drug interactions relative to the respective inhibitor compounds (NCEs) and respective CYP-specific probe substrates;

wherein steps c–f are repeated for a pre-determined number of times as individual test runs, with pre-thawed microsome samples, wherein, simultaneously with the steps of paragraphs c–f of one run, additional microsomes are removed from the freezer unit, thawed, and held at a holding site, for immediate use in steps c–f of a subsequent test run, wherein timing of when the frozen microsome are initially removed for thawing during steps c–f is such that removal is at the same point in time during said steps of each of the individual test runs and wherein duration of thawing and any pre-incubation is the same for all of the runs and incubation periods are pre-calculated and adapted to be of the same duration in each of said pair of plates during a test run, with the processing of plate pairs, while the first plate is in the first incubator, steps a–f are immediately repeated for the second plate of the first pair of the test run, with the pre-thawed microsome samples. In all cases, simultaneously with the steps of paragraphs a–f of one run (for the unit or for either of the pair as applicable), additional microsome samples are removed from the freezer unit, thawed, and held at a holding site, for immediate use in steps a–f of a subsequent test run. The timing of when the frozen microsome are initially removed for thawing during steps a–e is such that this removal is at the same point in time during said steps of each of the next test runs. In addition, duration of thawing is substantially the same for all of the runs and furthermore, to maintain synchronous operation, all pre-incubation (if any) and incubation periods are pre-calculated and adapted to be of the same duration per test run of unitary or pair of plates as applicable. It is understood that additional numbers of closely simultaneously processed plates per test run are simply scaled and timed accordingly.

After a single plate has been incubated or for a paired plate embodiment, once plate two has been returned to the incubator, the plates are then processed in series as described in steps g–i:

g) pre-determined amounts of the reaction products are mechanically transferred into individual wells of a multiwell filtration plate, and any reaction product is obtained such as by vacuum filtering; and the collection plate is covered and stored for subsequent analysis testing.

h) Step g is repeated for the second plate of a plate pair, as applicable.

i) Steps a–i are then repeated for any subsequent units or pairs of plates for drug-drug interaction testing.

After steps a–i are completed for all unitary or pairs of plates for drug-drug interaction testing, the stacked filtration collection plates are removed from the automated work station and the individual filtrates of the reaction products are sent for an analysis such as an $IC_{50}$ or Ki test for determining the extent of any drug-drug interactions.

The testing preparation device of the present invention which is utilized to effect the above steps comprises a computer controlled and coordinated device having:

a) a freezer unit for storing microsomes or recombinant microsomes;

b) a thawing unit or site for thawing said microsomes prior to use of the microsomes in the preparation of testing samples (the thawing unit may also comprise a portion of the freezer which is capable of being heated to a thawing temperature);

c) timed computerized means for removing frozen microsomes from the freezer unit to the thawing unit for the thawing of the microsomes (or for conversion of the freezer unit to a thawing unit without removal);

d) means for the buffering of the microsomes and with addition of co-factor to the microsomes, such as with fluid introduction means which transfers a preset quantity of microsomes into a trough containing co-factor materials and buffer (M/C/B trough) and mixing means for the homogeneous mixing of microsomes, buffer and cofactor in said trough;

e) a computer controlled and timed manipulation and transport mechanism for the holding, transporting and removal of multi-well test plates to and from operational stations of said device and for positioning of the plates at said operational stations for appropriate operation thereat, with said test plates being any one of reaction plates, filtration plates and collection plates;

f) a first operation station with fluid introduction means for simultaneously filling a plurality of predetermined wells of a reaction plate with a preset quantity of M/C/B;

g) a second operation station for optionally pre-incubating MIC/B to a pre-determined elevated temperature for a pre-determined period of time, to facilitate subsequent reaction time;

h) a third operation station for combining microsomes in wells of said reaction plate with a cytochrome P450 enzyme substrate and an inhibitor compound (S/I);

i) a fourth operation station for incubating said combination in said reaction plate in step h) to a temperature of about 37° C. for reaction thereof for a pre-determined period of time;

j) quenching means for stopping said reaction after said pre-determined period of time;

k) transfer means for transfer of reaction products from the wells of said reaction plate to wells of a filtration plate;

l) filtration means such as a vacuum for filtering the reaction product;

m) computerized timing means for synchronizing simultaneous operations with respect to each of the plates and the respective contents in the wells thereof, as well as timing of the thawing and pre-incubation, as appropriate, and incubation periods and initiation of thawing of microsomes for a subsequent test run;

n) a station for tracking test plates and contents thereof such as by reading a bar code identification to track each plate;

o) a holding area for each pre-thawed vial of microsomes for use in subsequent test runs;

p) the device further preferably comprises storage areas for maintaining plates for use in a pre-determined number of runs, with the respective plates being accessible by the manipulation and transport mechanism.

Solution transfer means are preferably embodied in multiple tip cannulas or pipettes which perform multiple aliquot operations.

It is understood that the term "filling" refers to the act of filling and is not to construed as a completion of filling the entire volume of any well. The use of 37° C. for incubation is relative to use of the present invention with human DDI testing and other in vivo emulation conditions are determined relative to the particular mammal.

The above objects, features and advantages of the present invention will become more evident from the following discussion and drawings in which:

SHORT DESCRIPTION OF THE DRAWINGS

DETAILED DESCRIPTION OF THE INVENTION

Figure 1:
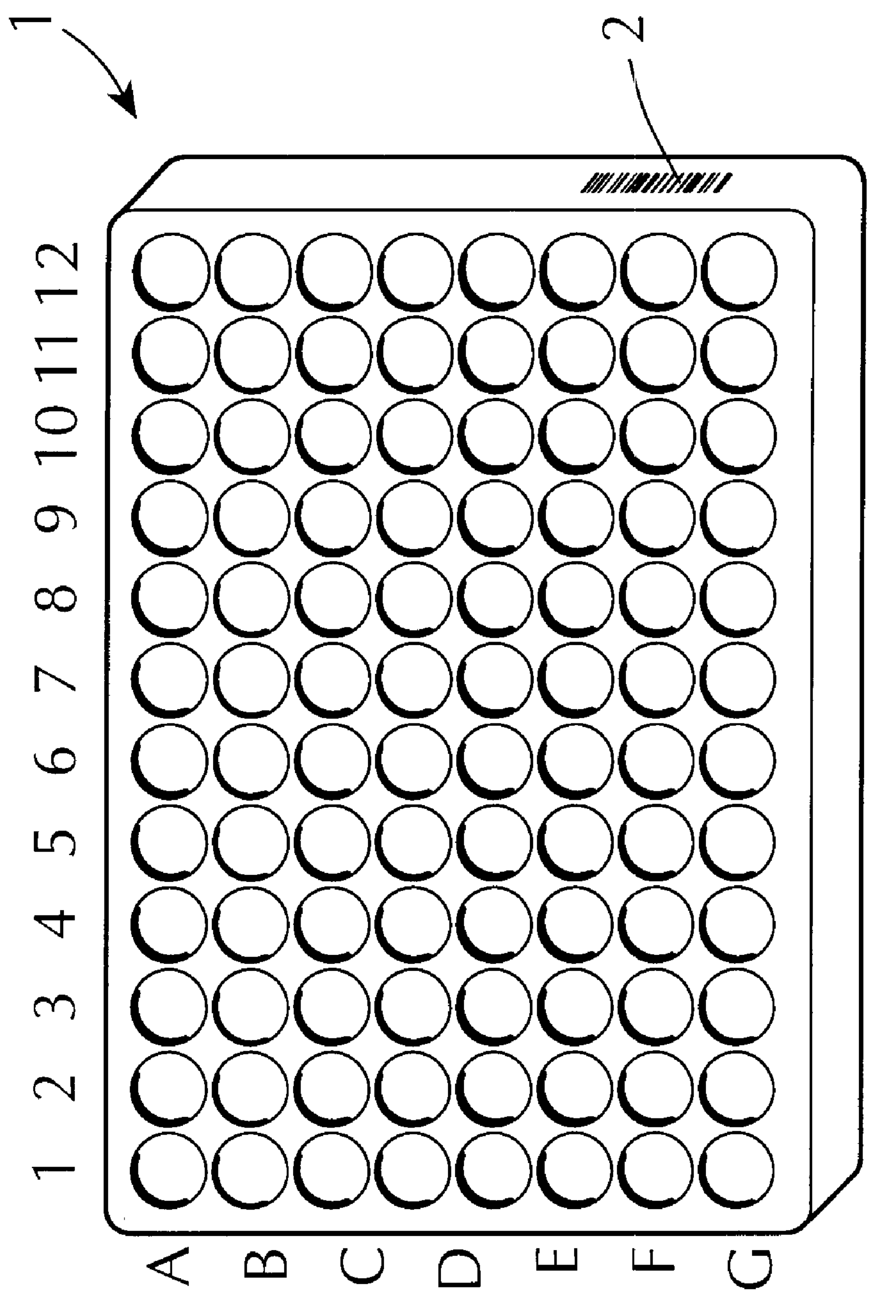
FIG. 1 is a top view of a typical 96 well testing tray or plate as used in the present invention.

In a typical test pre-preparation, with standard 96 well test plates (12×8 well arrangement), 50 microliters of new inhibitor compound (NCEs in a 0.12 millimolar solution), are individually aliquoted into a pre-determined well, together with one or a combination of five cytochrome P450 substrates (five different cytochrome substrates being extant and commercially available) in a solution comprised of an equi-volume mixture of methanol and water (this solvent mixture simply being exemplary of a preferred solvent, with other solvents being similarly utilizable). Each new compound (NCE) is prepared for testing with such aliquoting into one test preparation well in five different plates (for tests with each of the above five cytochrome substrates). Each plate comprises two associated controls comprised of the CYP-specific probe substrate with an inhibitor compound of known properties. Typical testing is, for example, for determination of a $IC_{50}$ or Ki value as a relative indication of drug interactions.

The above permutation of plates and respective wells is that of different compound (NCE) per each well with a single or combination of CYP-specific probe substrates for each plate. Other permutations are possible, with individual well compositions being carefully tracked. The prepared plates, all having unique individual bar code identification, are set aside for use during the actual test run preparation and testing.

The device of the present invention is essentially a programmed robot processing device (with known and commercially available individual component parts) which is provided with movable plate retaining means for movably simultaneously holding at least two test plates at a time (the number of plates being held is a function of efficiency and capability of being time coordinated) in a horizontal plane with test wells of the plates being accessible from above (for access in filling and mixing operations and to prevent spillage). The device further comprises incubation means (e.g., a temperature controlled heating element) for heating stored, refrigerated or frozen solutions of the compound (NCEs) to be tested, substrate enzyme material and microsomes, to an equilibrium temperature of about 37° C. (human body temperature). A transport mechanism with releasable plate gripping elements, for movement of microsome containing vials, from freezer to thawing position, is further included in the device, as is means for bar code reading and plate tracking.

A software controlled computer operation synchronizes and tracks the simultaneous preparation of microsomes, with removal from freezer, thawing to 4° C., aliquoting the microsomes, adding buffer to the microsome trough, mixing the microsomes with buffer (phosphate at pH 7.4) and co-factor (NADPH) for activation (M/C/B); with preparation (or preferably pre-preparation) of the five probe-specific substrates and inhibitor compounds (NCEs), in specific ratios and overall amounts, as well as controls with CYP-specific probe substrate but no inhibitor compound, or with inhibitor of known properties.

In an overall pre-preparation process, separate plates are initially prepared for the substrate enzymes and for dilutions of the inhibitor compound (NCEs). The contents of the two plates are then combined in a 1:1 ratio to make a master plate of Substrate and Inhibitor solution (S/I plate) used during the test preparation runs.

The remaining assay ingredients, a combination of Microsomes, Cofactor and Buffer (M/C/B), are prepared at 4° C. in an open trough and transferred to a reaction plate (typically having 96 wells and being comprised of an inert polypropylene material). Well dimensions are a function of the total number of wells and are minimally sized to at least hold requisite amounts of solution for processing and/or later testing as well as being sufficiently large to accommodate cannula tip insertion.

The reaction plate is pre-warmed to 37° C., and the reaction in each well is initiated by addition of an aliquot thereto from the S/I plate. The reaction is allowed to proceed at 37° C. The reaction is terminated, filtered and the samples are prepared for analysis on an HPLC and/or Mass Spectrometer. Peak areas of the metabolite of the probe substrate are measured by mass spectrometer, UV or florescence detection and analyzed using software available from the McQuan corporation.

The following example of a process used in preparation of an inhibitor compound with CYP1A2 specific probe substrate in a test sample is illustrative of the procedure of the present invention.

PROCESS

The following is a chronological order of the steps of a preferred method and system of the present invention. As described, the method enables the preparing for and effecting of $IC_{50}$ or Ki tests of 90 different inhibitor compounds (NCEs) (of a single test plate) with one or more probe CYP enzyme substrate and microsome samples within the space of one half an hour or with all five CYP enzymes (with five test plates in duplicate) within about five hours. Proportionate operations are adaptable for plates with different number of wells.

Pre-operation Preparation Steps Comprise:

1. The preferred device of the present invention comprises chilling and freezing unit elements for minimizing degradation of microsomes and enzymes. As a first step in the preparation for operation of the device, chilling re-circulator elements (with contained refrigerant) are allowed to reach a set temperature (the device is computer controlled and all monitored temperatures are shown on a computer screen).

2. Heater elements, for incubation of the test materials to human body temperature (37° C.), in the device are allowed to reach a set temperature above 37° C. (for incubation to the requisite body temperature). The elements are computer controlled and all monitored temperatures are shown on a computer screen.

3. A pipetting system in the device, with 96 permanent cannulas, for mixing and dispensing specific probe substrate and inhibitor compound (NCEs) is activated (referred to herein as "Robbins Hydra" for the commercially available source thereof.

4. A reservoir trough is loaded with cofactor.

5. A solution reservoir, used to quench reactions during the process, is filled with quenching solution (generally a solution of methanol and water).

6. Lines through which liquid is transported in the system are all primed with purging of retained air.

7. A workstation of the device (set up for five pair of test runs) is provided with:

10 uncapped Cryovials (#1–10) containing frozen microsomes, in a freezer holding region of the device, for providing the microsomes as needed.

Two aspirating pipettes with disposable sterile pipette tips (one pipette having 12 cannulas and one having 1 cannula)

10 reaction plates (#1–10)

10 S/I Plates (the wells thereof having been pre-provided with measured amounts of the specific Substrate CYP enzyme/inhibitor compounds (NCEs))#1–10

10 Filter (Multi-screen) Plates (#1–10)

10Collection Plates (#1–10) with a cover in the cover nest

The workstation contains storage areas for holding of the plates until use thereof is required and a selecting and transporting mechanism is used to select the plates as needed and transport them to operational stations of the device. The number of plates of each type and the number of wells (e.g. 96) in each should be the same. The number of plates is a function of the number of tests to be run without re-loading.

After the above preliminary preparations are effected, a sample preparation and testing run is initiated with the following time coordinated steps:

1. Cryovial #1, containing microsomes in a buffer solution, is transported within the device from Frozen to Thaw position (i.e., removed from the freezer site) by an automated mechanical transport mechanism.

2. Reaction Plate #1 is selected from the storage site and moved to a waiting position ("transfer nest").

3. After the microsomes have completely thawed for at least 8 minutes (minimum time for complete thawing) and, for synchronization, an additional time which would provides a thawing time, equal for all ten of the cryovials during the run; the single cannula, with disposable pipet, is moved to Cryovial #1 to mix the microsome solution. The pipette is used to mix the microsome solution by aspirating a partial volume thereof and returning the partial volume to the Cryovial for any number of times, as required in a mixing protocol.

4. Synchronized thawing time is determined based on the steps required in the testing run. For a ten vial system, and with the parameters enumerated in the present example, synchronized thawing time for each Cryovial is 15 minutes.

5. A pre-determined microsome volume is aspirated by the single cannula and dispensed into Trough #1 (of ten troughs).

6. Another single cannula is moved to aspirate a pre-determined buffer (with cofactor) volume from the buffer reservoir and then moved to dispense the buffer volume into Trough #1.

7. The 12 cannula pipette (with disposable pipette tips) is moved to Trough #1 to aspirate the diluted microsome volume to mix the M/C/B. The station then rocks to mix the contents of the trough. The 12 cannula pipette (with disposable pipette tips) is moved to Trough #1 to aspirate the diluted microsome volume and then is moved to the transfer nest to dispense the diluted microsome volumes to the Reaction plate (96 wells, 8 rows with 12 wells/row) in the first four rows thereof.

8. Step 7 is repeated to fill rows E-H of the reaction plate #1.

9. The filled reaction plate #1 plate is then transported to a Heater site for a "Pre-incubation Time" sufficient to raise the temperature of the contained microsome solution to a pre-determined temperature and Reaction Plate #1 "Pre-Incubation Start Time" is recorded." The 12 pipette and single pipette cannulas are cleaned for re-use during the test run (they are replaced for different test runs). The pre-incubation time is adjusted to be the same for each reaction plate in the test run. (Cryovial #2 is moved at about this time from frozen to thaw position. Actual time of such movement is determined based on equivalent time for each of the reaction plate runs.)

10. A pre-prepared 96 well S/I Plate #1 is picked up and transferred to the Robbins Hydra 96 pipette system using a second gripper arm capable of moving plates outside the deck work space. The prepared S/I plate contains 90 wells filled with 90 different inhibitor compounds (NCEs) for testing and specific probe substrate(s) in all the wells. Two wells contain the specific probe substrate with an inhibitor compound of known characteristics, as control, and four wells contain a control of only a 50/50 methanol/water solvent (alternative permutations, such as one inhibitor compound with the five CYP enzyme substrates are similarly possible).

11. Each plate used in the process is provided with a unique identifying bar code and the S/I plate bar code is read at the pipette system site for later identification and correlation of the compounds contained therein.

12. An "S/I Volume" of the 90 compounds and controls is aspirated by the Robbins Hydra pipettes and S/I Plate #1 is transported first to the bar code plate nest and then is moved to the S/I Plate "empty" stack area (about 10–25% of the volume of the wells is aspirated with material remaining in the wells being available for additional tests, if necessary).

13. After the pre-determined "Pre-incubation Time" for reaction plate #1 has ended, it is transported to the Robbins Hydra pipette system (with the "Pre-Incubation End Time" being recorded) via the bar code nest and second arm. The aspirated S/I volume is dispensed by the pipettes into the corresponding wells of reaction plate #1 and mixed once.

14. Reaction Plate #1 is then return transported to the Heater for an "Incubation Time" and the "Reaction Plate #1 Incubation Start Time" is recorded. The incubation time is sufficient to attain an ambient reaction temperature of 37° C. and is of a duration which is pre-calculated to be the same for each pair of reaction plate incubations in the overall test run.

15. During the "reaction" of the "Reaction Plate" #1:

Steps 5–14 are repeated for Reaction Plate #2. Once reaction plate #2 been returned to the Heater for the same "Incubation Time" as plate #1 then the "Reaction Plate #2 Incubation Start Time" is recorded.

16. The automation process then sets up Plate #1 for filtration:

The Hydra 96 pipette system is rinsed clean and transported to the Quench Solution Trough, where a "Quench Volume" is aspirated;

Collection Plate #1Cover is removed and placed in holding position at a Cover Nest:

Collection Plate #1 bar code is read for correlation of well samples and the Collection Plate #1 is picked up and moved to the bottom of a vacuum filtration chamber, the vacuum chamber cover is closed and Filter Plate #1 is picked up and moved to the top of the vacuum chamber.

17. When "Incubation Time" for Reaction Plate #1 has expired, Reaction Plate #1 is removed from Heater #1 and placed at the 96 pipette system where a "Quench Volume" is dispensed into Reaction Plate #1 (i.e., each of the wells):

18. The Reaction Plate #1 is transferred to the Transfer Nest where a "Sample Volume" is aspirated by the 12 pipette cannula from Row A of Reaction Plate #1 and the "Sample Volume" is dispensed to Row A of Filter Plate #1.

19. The 12 pipette cannula is washed and step 17 is repeated for all the rows A–H.

20. A vacuum is turned on for the filtering plate for a pre-determined "Filtering Time" and then turned off (Reaction Plate #1 and Filter Plate #1 are discarded) and Collection Plate #1 is moved to a holding stack (where the collection plate cover #1 is replaced).

21. Cryovial #(current +2), containing microsomes, is moved from Frozen to Thaw position so that the microsomes therein will be ready when or shortly after the transport mechanism is finished with the current process, e.g., when processing plate #1, cryovial #3 will be moved. (This step should be executed at the point during the process which produces consistent or equivalent thawing times for all 10 cryovials).

22. Steps 16–21 are repeated for Reaction Plate #2. Then the process is repeated for all the remaining microsome samples and reaction plates in a paired fashion.

A typical run utilizing 96 well plates is of a duration of about one hour, within the time frame of microsome degradation. As described, 90 compounds can be tested in duplicate with a single specific probe substrate in a one hour span and with all five CYP enzymes in about five hours. Thus, close to 1000 compounds can be effectively tested for DDI during a typical five day work week with the single point determination described in said co-pending provisional application. Use of larger plates such as 384 or even 1536 wells can substantially increase the testing yield with concomitant upgrading of aliquoting pipettes and software tracking, subject to processing time coordination.

In the above-described procedure, concentration ranges and amounts used of components are typically as follows:

a) 0.01 μM–100 μM in a final incubated concentration for inhibitors and 2 mM for specific probe substrates, both in separate 50/50 methanol-water solutions.

b) 50 μl is aspirated from each of the inhibitor compound and substrate solutions, and pipetted into a well of a 96 well S/I plate (proportionately lesser amounts are used in plates with larger number of wells) and mixed 3 times by successive 50% volume aspirations and returns. The pre-prepared S/I plates are covered and stored at 4° C. for no more than 5 days prior to use.

c) The Microsomes/Cofactor/Buffer mix (M/C/B) follows the following recipe:

i) NADPH-regenerating cofactor solution=10% (v/v).

ii) microsome=0.1–0.5 mg/ml protein concentration iii) Remainder of volume is made up with 100 mM sodium phosphate buffer, pH 7.4.

iv) The microsomal protein is added just prior to use for maximum utilization while it remains stable.

d) During use, 190 μl M/C/B are transferred from the reservoir trough to a well of the reaction plate. Pre-incubation brings the temperature to 37° C. and generates $NADPH^+$.

e) 10 μl are transferred from the pre-prepared S/I plate to each of the wells of the reaction plate.

q) 20 μl of 50/50 methanol/water serve for example as a reaction stop when added to the reaction plate r) For testing, 100 μl of the reaction products are taken from the reaction plate to a 96-well Multiscreen-HA filter plate (automation provides for different volumes). Samples are slowly drawn through the filter plate by a weak vacuum and collected in a polypropylene 96-well collection plate.

s) 5–30 μl for HPLC/MS analysis, with injections made every 30 sec to 4 min.

DETAILED DESCRIPTION OF THE DRAWINGS AND THE PREFERRED EMBODIMENT

With reference to the drawings, and to the above procedure, FIG. 1 depicts a 96 well plate 1, for which the test preparation device 10 (in FIGS. 2–3) is adapted for use. It is understood that modifications of the device are correlated to the well plate being specifically used, and the number of wells therein, such as the 96 illustrated, as well as 384 (4×) and 1536 (16×) wells, with concomitantly enhanced through-put and processing requirements, as described above.

Well plates 1 are used:

a) for containing compound/substrate (S/I plate 1*a*), usually in pre-prepared form, to individually supply inhibitor compound and enzyme for reaction with liver microsomes;

b) as a reaction site (reaction plate 1*b*) where the compound, enzyme and microsome are incubated and reacted;

c) for filtration, (filtration plate 1*c* with porous well bases) with reaction products being transferred to the filtration plates for vacuum filtration; and d) for collection of vacuum filtered reaction products for the subsequent DDI testing (collection plate 1*d* with cover 1*e*) with analysis devices such as HPLC and/or mass spectrometers.

All the plates preferably have the same number of wells for each purpose, e.g., 96, in the plate shown, as well as the same overall dimensions for facilitated material transfer as well as for facilitated transport and handling (multiple aspiration and aliquoting generally requires identical relative placement of wells for proper operation). In addition, each well plate has a unique bar code identification 2 to keep track of all the plates, with correlation to plate function and to correlate identification of compounds being tested and particular enzyme combination, with preparation stages, pre-selected parameters and subsequent test results.

In the well plate 1 shown, specific wells are identified by an alphanumeric labeling intersection of 8 down rows A–H and twelve columns 1–12. The plates are comprised of inert materials such as of polypropylene and are essentially the same except for the filtration plates, which embody porous filtering elements at the base of the individual wells.

Figure 2:
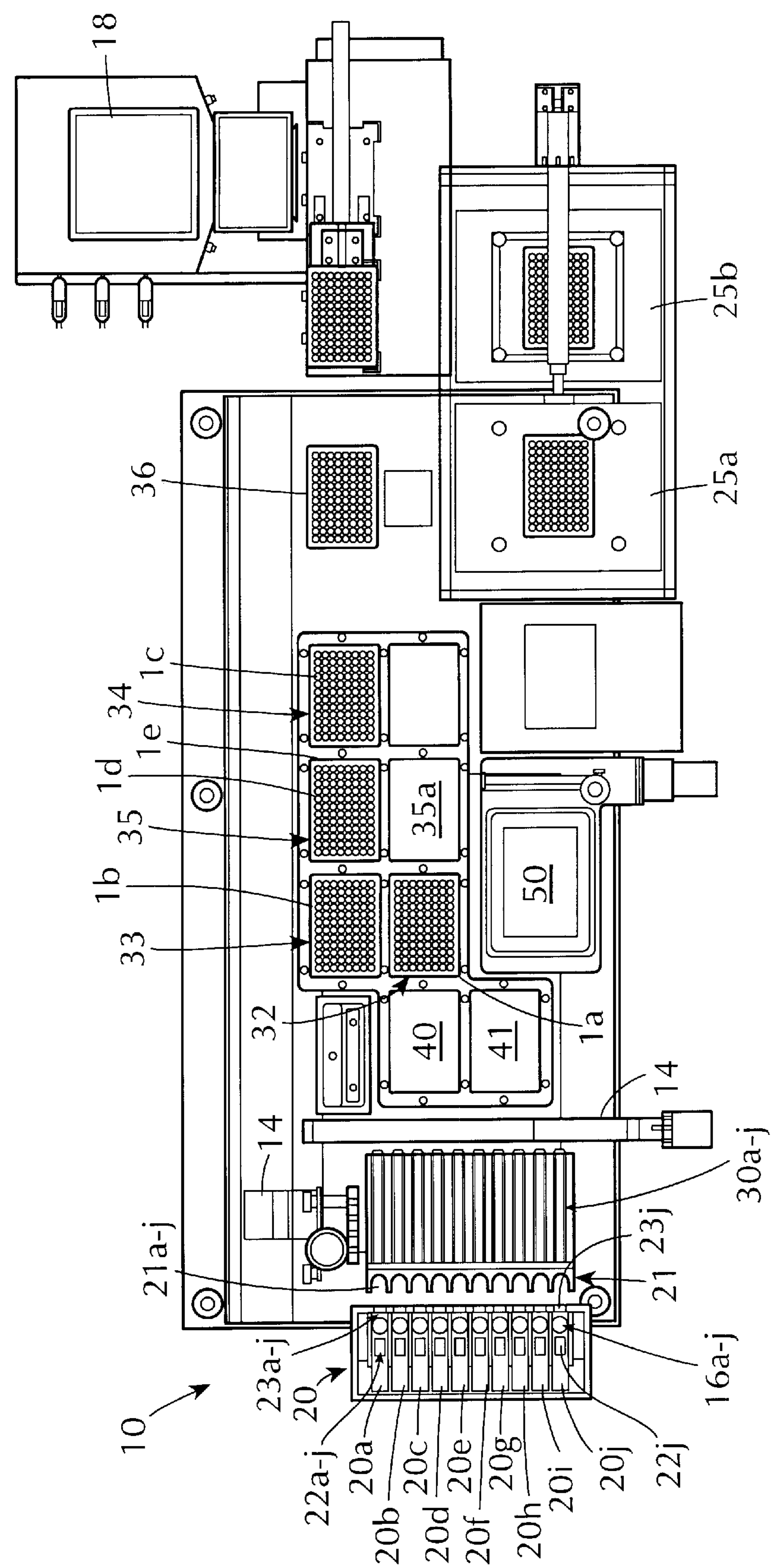
FIG. 2 is a top view of the device of the present invention.
Figure 3:
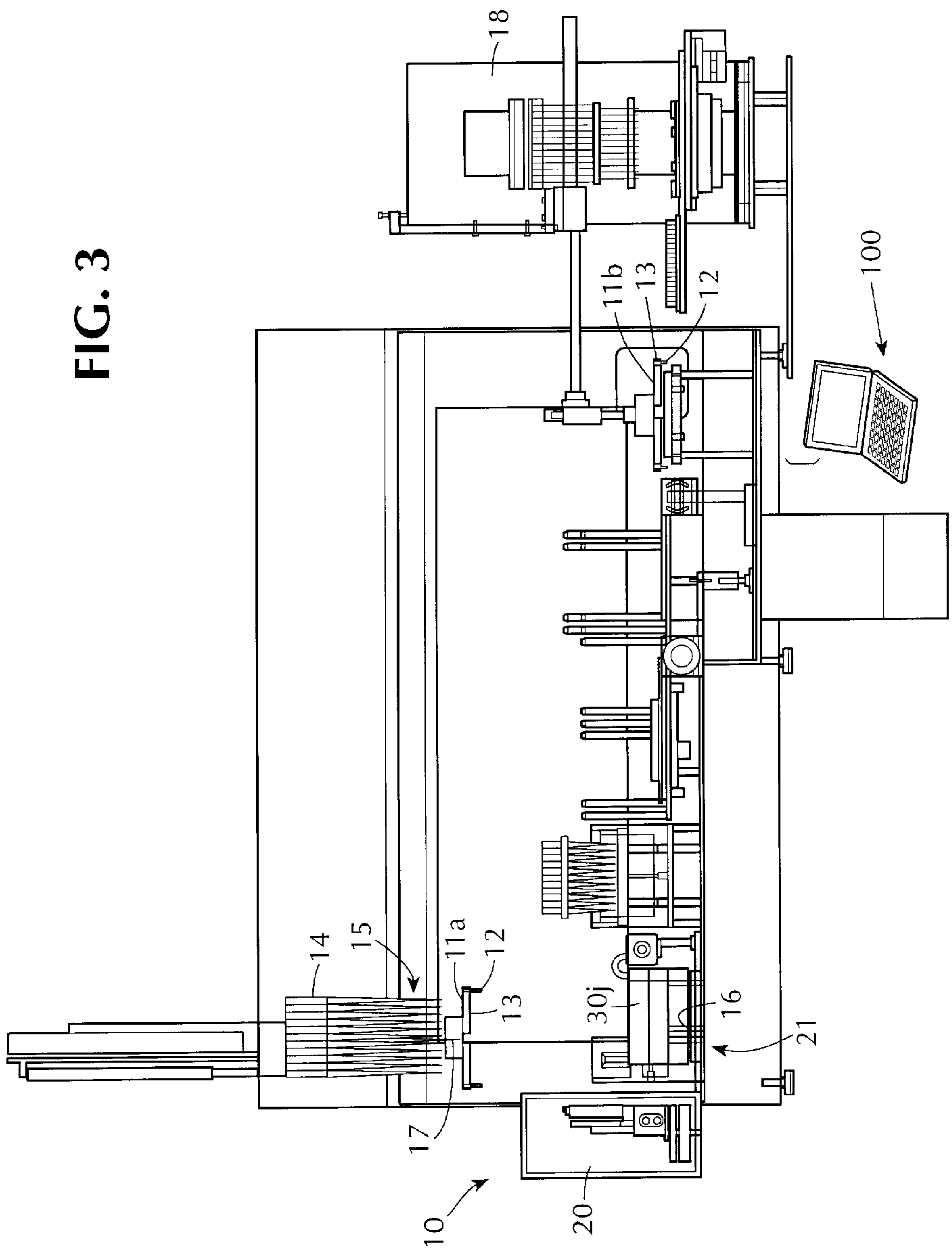
FIG. 3 is a front view of the device of the present invention.

The test preparation device 10, shown in FIGS. 2–3, is adapted for five pairs of test runs (with a total of 40 well plates for all of the test plate types) without reloading of elements.

Prior to the start of the initial test preparation run, ten plates of each type are stacked at the respective sites: site 33 for retention of reaction plates 1*b*, site 32 for retention of the S/I plates 1*a*, site 34 for the filter plates 1*c* and site 35 for the collection plates 1*d* with covers 1*e*. The S/I plates 1*a* are each preloaded with pre-determined combinations of inhibitor compounds and CYP enzymes in 90 of the wells thereof with 6 wells functioning as controls without inhibitor compounds or with compounds of known interactive characteristics.

Freezer unit 20, with 10 chambers 20*a–j*, and maintained at −20° C., is loaded with 10 uncapped cryovials 16*a–j*, containing human liver microsomes and 10 open troughs 30*a–j*, are filled with pre-determined concentrations of buffer solutions with cofactor. Thawing station 21, maintained at 4° C., is directly adjacent freezer unit 20 with cryovial holding members 21*a–j*. Transfer of cryovials from the freezer unit to the thawing station is effected by opening of the appropriate freezer unit chamber door (one of doors 23*a–j*) and ejection pushing of the selected cryovial, by the appropriate ejection finger 22*a–j*, into the adjacent holding member 21*a–j*.

Cannula unit 14, functions to initially:

a) provide material transfer of thawed microsomes from the cryovials to the adjacent buffer-cofactor troughs;

b) provide material transfer of M/C/B (microsome/cofactor/buffer) from the trough to a selected reaction plate.

Cannula unit 14 comprises a row 15 of twelve stainless steel cannulas, with manually replaceable pipette tips, sized dimensioned and arranged for operable engagement with a full row 1–12 of well plates 1. Cannula unit 14 further includes a separate single stainless steel cannula 17 and replaceable pipette tip for use in transfer of thawed microsomes from any one of cryovials 16*a–j*, to an adjacent M/C/B trough. Because of the nature of the microsomes as a degradable bio-material, disposal of pipette tips is preferable to sterilization. Cannula unit 14 is movable relative to the cyrovials and troughs to effect the appropriate transfers.

Plate transport elements 11*a* and 11*b* each comprises four releasable test plate grippers 12 on an expanding and contracting support 13 for picking up, holding, and releasing plates 1 and moving them in an X-Y-Z transport direction as required to any and all of the processing stations of the device (where they are released or held for further transport). Grippers 12 are laterally extensible with contraction and expansion of the support 13, to thereby grip and release plates. Transport elements 11*a* and 11*b* overlap in site movement capability and range, with element 11*a* transporting trays to and from plate storage areas (32–35), bar code reader 36, incubators 25*a* and 25*b*, nests 40 and 41 and vacuum chamber 50 while element 11*b* transports trays to and from the hydra 18, bar code reader 36, incubators 25*a* and 25*b* and vacuum chamber 50.

The test plates are maintained parallel to the ground with the respective wells being open, away from the ground, for effective filling and liquid maintaining purposes.

The test preparation device 10 comprises a fixed position Robbins Hydra unit 18 with 96 cannulas capable of aspirating and dispensing measured amounts of solution material into each of the wells of a plate transported by transport element 11*b* into alignment therewith. The Hydra unit 18 is used to aspirate and dispense S/I solutions from an S/I plate into a reaction plate containing M/C/B and to mix reactants.

In operation, a cryovial is removed from the freezer unit and thawed with microsomes contained therein being transferred via the single cannula 17 to a trough (30*a–j*, as appropriate) for mixture with cofactor and buffer. The trough array 30*a–j* is seated on a cam element 16' which effects a motorized gentle rocking to effect mixing and to ensure homogeneity of the M/C/B mixture. Transport element 11*a* selects a reaction plate 1*b* from the top of the stack at site 33 and transports it to transfer nest 40. Cannula row 15 of cannula unit 14 aspirates M/C/B mixture from one of troughs 30*a–j*, (as appropriate) and moves to fill wells of the reaction plate 1*b* row by row. The reaction plate 1*b* is then transported by transport element 11*a* to one of heaters 25*a* or 25*b* for a pre-incubation period (for a time pre-determined to be equal for all the test runs).

While the first plate is incubating, a second reaction plate of the testing pair is similarly filled with the M/C/B mixture and pre-incubated in the other of heaters 25*a* and 25*b*. After the pre-incubation, an S/I plate is transported by transport element 11*b* to the hydra unit 18 where the pre-loaded inhibitor compound and CYP enzyme solutions are aspirated by the 96 cannula pipettes. The S/I plate is removed to restack or empty plate position 35*a* and the first filled M/C/B reaction plate is transported to the Hydra 18 for filling with the respective compound solutions to initiate a reaction and the reaction plate is thereafter returned to a heater for incubation to human body temperature of 37° C. The second plate of the pair is similarly subjected to reaction and incubation.

For both plates of the test pair, incubation and attendant reactions proceed for a pre-determined period of time (determined as described above). While the reaction plates are being incubated at the heaters the Hydra 18 aspirates a quench solution from a quench solution reservoir containing a solution such as a methanol and water solution suitable for quenching the reaction involving inhibitor compound, enzyme substrate and microsomes. A collection plate 1*d* is removed from site 35 and placed at the bottom of vacuum chamber 50 and the cover 1*e* is placed at cover nest. Filter plate 1*c* is removed from the stack at site 34 and placed at the top of the vacuum chamber 50.

After a pre-determined incubation period, the first reaction plate is transported from the respective heaters to the Hydra 18 which dispenses the aspirated quench solution to the reaction wells of the reaction plate to stop all reactions therein. The reaction plate is removed by transport element 1*b* from the Hydra site and placed on transfer nest 40 where cannula element 14 with row of pipettes 15 sequentially aspirates and dispenses measured reaction product solutions from rows A–H of the reaction plate to corresponding wells of the filter plate 1*c*, in the vacuum chamber, until all the rows have been filled as pre-determined.

The vacuum chamber is activated to effect filtration of reaction material to the collection plate 1*d*. The filter plate and reaction plates are removed and the collection plate is removed, covered and stored or sent for analysis of reaction products and extent of DDI.

The quenching and filtration process is repeated for the second plate.

Bar code reader 36 situated between the Hydra 18 and the other stations of the device is used to track plates and wells passing within the scanner thereof particularly to correlate the identity of inhibitor compound and particular CYP enzyme in identified wells of identified plates to results of subsequent tests and analysis.

Computer 100 provides control of the sequential and simultaneous (e.g., thawing of microsomes for subsequent test runs) timed operations as well as keeping track of process conditions and bar code identification with parameters of the process such as incubation temperatures and the like being displayed on a computer monitor. The computer also permits input changes of operations such as may be necessary with change of number of test runs, number of wells and even species of mammal for which DDI are being tested.

It is understood that the above examples and drawings are illustrative of the method and device of the present invention and that changes in materials and types of DDI (e.g., applicability to mammals other than humans with appropriate enzymes and microsomes as well as in vitro condition emulation) structure, steps and components may be made without departing from the present invention as defined in the following claims.

What is claimed is:

1. A method for preparing inhibitor compounds for in vitro testing of in vivo drug-drug interactions in mammals, wherein the method comprises the automated steps of:

a) retrieving frozen microsomes of a mammal species from a freezer storage unit;

b) thawing the retrieved frozen microsomes;

c) mechanically introducing a pre-determined quantity of (i) the thawed microsomes, (ii) a cofactor, and (iii) a buffer into individual wells of a multiwell reaction plate and pre-incubating the reaction plate with contained microsomes to an in vivo temperature for said mammal for a pre-determined period of time;

d) mechanically combining the thawed microsomes in each of the wells of the reaction plate with a pre-determined quantity of a combination of one of said inhibitor compounds and a preselected probe substrate specific for cytochrome P450s (CYP);

e) incubating the reaction plate with contained microsomes, CYP-specific probe substrate and inhibitor compounds to said in vivo temperature for a pre-determined period of time, to effect reaction in the individual wells, with resultant respective reaction products;

f) stopping any reactions which occur, at the end of the pre-determined period of time, purifying the reaction products and using the reaction products in an analysis test for determining the extent of any drug-drug interactions relative to the respective inhibitor compounds and respective CYP-specific probe substrate;

wherein steps c–f are repeated for a pre-determined number of times as individual test runs, with pre-thawed microsome samples, wherein, simultaneously with the steps of c–f of one run, additional microsomes are removed from the freezer unit, thawed, and held at a holding site, for immediate use in steps c–f of a subsequent test run, wherein timing of when the frozen microsomes are initially removed for thawing during steps c–f is such that removal is at the same point in time during said steps of each of the individual test runs and wherein duration of thawing and any pre-incubation is the same for all of the runs and incubation periods are pre-calculated and adapted to be of the same duration for each paired set of plates during a test run.

2. The method of claim 1, wherein the mechanical introducing is effected with multiple cannula elements automatically operable with computer controlled aspiration and dispensing of fluid solutions.

3. A method for preparing inhibitor compounds for in vitro testing of in vivo drug-drug interactions in mammals, where the method comprises the automated steps of:

a) retrieving frozen microsomes from a freezer storage unit with an automated mechanical transport mechanism;

b) thawing the frozen microsomes;

c) automatically mechanically introducing measured amounts of the microsomes and buffer, into a receptacle trough, with cofactor;

d) automatically mechanically introducing equal amounts of the combination of thawed microsomes, buffer and cofactor, into individual wells of a multiwell reaction plate;

e) thereafter automatically mechanically transporting the multiwell reaction plate to a heating device for pre-incubation heating of the combination of thawed microsomes, buffer, and cofactor for a pre-determined period of time;

f) automatically mechanically introducing a mixture of a preselected CYP-specific probe substrate and an inhibitor compound solution to the combination of microsomes, buffer, and cofactor in the incubated multiwell reaction plate and mixing;

g) thereafter incubating the reaction plate to an in vivo temperature for said mammal for a pre-determined period of time;

h) stopping any reaction which may have occurred after said pre-determined period of time;

i) mechanically introducing pre-determined amounts of the reaction mixture into individual wells of a multiwell filtration plate, and vacuum filtering any reaction product therein;

j) using the reaction product in an analysis test to determine the extent, if any, of drug-drug interactions of said compound;

wherein steps c–j are repeated for a pre-determined number of times as individual test runs, with pre-thawed microsome samples; wherein, simultaneously with the steps of c–i of one run, additional microsomes are removed from the freezer unit, thawed, and held at a holding site, for immediate use in steps c–j of a subsequent test run; and wherein timing of when the frozen microsomes are initially removed for thawing during steps c–j is such that removal is at the same point in time during said steps of each of the individual test runs and wherein, duration of thawing is the same for all of the runs and all pre-incubation and incubation periods of all individual test runs are pre-calculated and adapted to be of substantially the same duration.

* * * * *